United States Patent [19]

Dawes et al.

[11] 4,172,080

[45] Oct. 23, 1979

[54] PHOSPHORUS ESTERS OF 1-CYANOETHYL-1,2,4-TRIAZOL-3-OLS

[75] Inventors: Dag Dawes, Muttenz; Beat Bohner, Binningen; Willy Meyer, Riehen, all of Switzerland

[73] Assignee: Ciba-Geigy Corporation, Ardsley, N.Y.

[21] Appl. No.: 527,330

[22] Filed: Nov. 26, 1974

[30] Foreign Application Priority Data

Dec. 6, 1973 [CH] Switzerland ................. 17192/73
Aug. 16, 1974 [CH] Switzerland ................. 11258/74

[51] Int. Cl.² .................... A01D 9/36; C07F 9/65
[52] U.S. Cl. ................... 548/118; 71/86; 71/87; 260/465.4; 424/200; 548/263; 548/264
[58] Field of Search ...................... 260/308 R

[56] References Cited

U.S. PATENT DOCUMENTS

| | | | |
|---|---|---|---|
| 3,686,200 | 8/1972 | Scherer et al. | 260/308 R |
| 3,809,701 | 5/1974 | Dawes et al. | 260/308 R |
| 3,862,124 | 1/1975 | Dawes et al. | 260/308 R |
| 3,862,170 | 1/1975 | Dawes et al. | 260/308 R |
| 3,867,396 | 2/1975 | Dawes et al. | 260/308 R |

*Primary Examiner*—Alton D. Rollins
*Attorney, Agent, or Firm*—Frederick H. Rabin

[57] ABSTRACT

New 1,2,4-triazoles, their manufacture and use as active ingredient on pest control is disclosed. The triazoles correspond to the formula

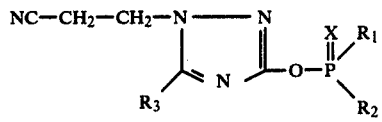

wherein
$R_1$ represents $C_1-C_6$-alkyl, $C_1-C_6$-alkoxy or $C_1-C_6$-alkylthio,
$R_2$ represents $C_1-C_6$-alkyl,
$R_3$ represents hydrogen, chlorine, bromine, $C_1-C_6$-alkyl, $C_1-C_6$-alkylthio, $C_3-C_5$-alkenylthio or $C_3-C_5$-alkynylthio, and
X represents oxygen or sulphur.

10 Claims, No Drawings

PHOSPHORUS ESTERS OF 1-CYANOETHYL-1,2,4-TRIAZOL-3-OLS

The present invention relates to derivatives of 1,2,4-triazole, to processes for their preparation, and to their use in pest control.

The 1,2,4-triazole derivatives have the formula

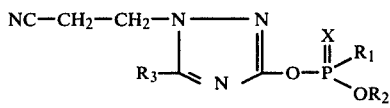

(I)

wherein $R_1$ represents $C_1$-$C_6$-alkyl, $C_1$-$C_6$-alkoxy or $C_1$-$C_6$-alkylthio, $R_2$ represents $C_1$-$C_6$-alkyl, $R_3$ represents hydrogen, chlorine, bromine, $C_1$-$C_6$-alkyl, $C_1$-$C_6$-alkylthio, $C_3$-$C_5$-alkenylthio or $C_3$-$C_5$-alkynylthio, and X represents oxygen or sulphur.

The alkyl, alkoxy, alkylthio, alkenylthio or alkynylthio groups denoted by $R_1$, $R_2$ and $R_3$ can be straight-chain or branched-chain. Examples of such groups are, inter alia: methyl, methoxy, methylthio, ethyl, ethoxy, ethylthio, propyl, propoxy, propylthio, isopropyl, n-, i-, sec.-, tert.-butyl, n-pentyl, n-hexyl and isomers thereof, allylthio, methallylthio and propargylthio.

Compounds of formula I especially preferred on account of their action are those wherein $R_1$ represents ethyl, ethoxy or n-propylthio, $R_2$ represents ethyl, $R_3$ represents hydrogen, methyl, methylthio or ethylthio, and X represents sulphur.

The compounds of formula I can be prepared by methods known per se; for example, they can be prepared as follows:

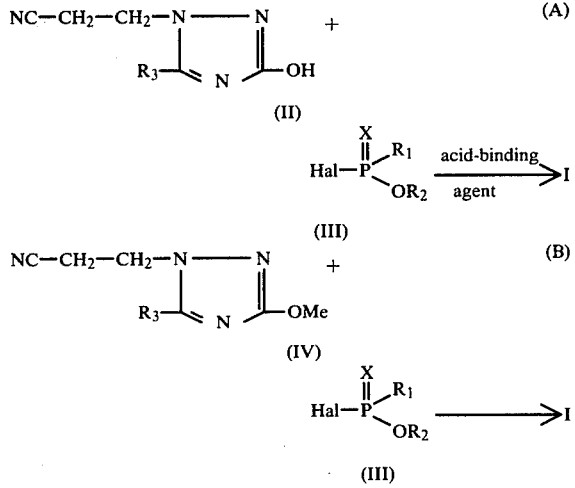

In formulae II, III and IV, the symbols $R_1$, $R_2$, $R_3$ and X have the meanings given for formula I, and Hal stands for halogen, preferably for chlorine or bromine, and Me stands for a metal, particularly an alkali metal, ammonium or trialkylammonium.

Suitable acid-binding agents are, for example, the following bases: tertiary amines such as triethylamine, dimethylaniline, pyridine, inorganic bases such as hydroxides and carbonates of alkali metals and alkaline-earth metals, preferably sodium and potassium carbonate.

The processes A and B are performed at a reaction temperature of between 0° and 120° C., preferably at between 20° and 80° C., at normal pressure and in solvents or diluents. Suitable solvents or diluents are, for example, ethers and ethereal compounds, such as diethyl ether, dipropyl ether, dioxane, dimethoxyethane or tetrahydrofuran; amides such as N,N-dialkylated carboxylic acid amides; aliphatic, aromatic as well as halogenated hydrocarbons, especially benzene, toluene, xylenes, chloroform or chlorobenzene; nitriles such as acetonitrile; dimethylsulphate, ketones such as acetone or methyl ethyl ketone, and water.

The starting materials of formulae II and IV are new but those of formula III are known. They can however all be prepared by processes analogous to known processes.

The compounds of formula I are suitable for the control of various animal and plant pests. They possess nematocidal properties and can be used; for example, for the control of phytopathogenic nematodes. In some cases, the active substances of formula I are suitable also as herbicides and as agents regulating plant growth, as well as for the control of viruses, bacteria and phytopathogenic fungi. They are effective however, in particular, against all development stages, such as eggs, larvae, nymphs, pupae and adults, of insects and members of the order acarina, such as mites and ticks.

The compounds of formula I have a lethal or repellent action against, for example, the following insects or members of the order acarina: insects of the families: Tettigonidae, Gryllidae, Gryllotalpidae, Blattidae, Reduviidae, Phyrrhocoridae, Cimicidae, Delphacidae, Aphididae, Diaspididae, Pseudococidae, Scarabaeidae, Dermestidae, Coccinellidae, Tenebrionidae, Chrysomelidae, Bruchidae, Tineidae, Noctuidae, Lymatriidae, Pyralidae, Gulicidae, Tipulidae, Stomoxydae, Trypetidae, Muscidae, Galliphoridae and Pulicidae; as well as acarids of the families: Ixodidae, Argasidae, Tetranychidae and Dermanyssidae. Particularly favourable effects are produced against rice pests.

The insecticidal and/or acaricidal action can be appreciably broadened and adapted to suit the given circumstances by the addition of other insecticides and/or acaricides. Suitable derivatives for example are, inter alia:

organic phosphorus compounds,
nitrophenols and derivatives thereof,
formamidines, pyrethrin-like derivatives,
ureas,
carbamates and chlorinated hydrocarbons.

The compounds of formula I can be used on their own or together with suitable carriers and/or additives. Suitable carriers and additives may be solid or liquid, and they correspond to the substances common in formulation practice, such as, for example, natural or regenerated substances, solvents, dispersing agents, wetting agents, adhesives, thickeners, binders and/or fertilisers.

For application, the compounds of formula I can be processed into the form of dusts, emulsion concentrates, granulates, dispersions, sprays or solutions, the formulation of these preparations being effected in a manner commonly known in practice.

The agents according to the invention are prepared in a manner known per se by the intimate mixing and/or grinding of active substances of formula I with suitable carriers, optionally with the addition of dispersing agents or solvents which are inert to the active substances. The active substances can be obtained and used in the following forms:

solid preparations:

dusts, scattering agents, granulates, coated granulates, impregnated granulates and homogeneous granulates;

liquid preparations:

(a) water-dispersible active-substance concentrates: wettable powders, pastes or emulsions;

(b) solutions.

The content of active substance in the described agents is between 0.1 and 95%.

The active substances of formula I can be formulated, for example, as follows:

Dusts:

The following substances are used in the preparation of (a) a 5% dust, and (b) a 2% dust:

(a)
5 parts of active substance,
95 parts of talcum;

(b)
2 parts of active substance,
1 part of highly dispersed silicic acid,
97 parts of talcum.

The active substances are mixed and ground with the carriers.

Granulate:

The following substances are used to prepare a 5% granulate:

5 parts of active substance,
0.25 part of epichlorohydrin,
0.25 part of cetyl polyglycol ether,
3.50 parts of polyethylene glycol,
91 parts of kaolin (particle size 0.3–0.8 mm).

The active substance is mixed with epichlorohydrin and dissolved with 6 parts of acetone; the polyethylene glycol and cetyl polyglycol ether are then added. The solution thus obtained is sprayed onto kaolin, and the acetone is subsequently evaporated off in vacuo.

Wettable powder:

The following constituents are used for the preparation of (a) a 40%, (b) and (c) a 25%, and (d) a 10% wettable powder:

(a)
40 parts of active substance,
5 parts of sodium lignin sulphonate,
1 part of sodium dibutyl-naphthalene sulphonate,
54 parts of silicic acid;

(b)
25 parts of active substance,
4.5 parts of calcium lignin sulphonate,
1.9 parts of Champagne chalk/hydroxyethyl cellulose mixture (1:1),
1.5 parts of sodium dibutyl naphthalene sulphonate;
19.5 parts of silicic acid,
19.5 parts of Champagne chalk,
28.1 parts of kaolin;

(c)
25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminium silicate,
16.5 parts of kieselguhr,
46 parts of kaolin;

(d)
10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to prepare (a) a 10% and (b) a 25% emulsifiable concentrate:

(a)
10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene;

(b)
25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

From these concentrates it is possible to prepare, by dilution with water, emulsions of any desired concentration.

Spray:

The following constituents are used to prepare (a) a 5% spray and (b) a 95% spray:

(a)
5 parts of active substance,
1 part of epichlorohydrin,
94 parts of ligroin (boiling limits 160°–190° C.); or (b)
95 parts of active substance,
5 parts of epichlorohydrin

EXAMPLE 1

Preparation of
O,O-diethyl-O-[1-cyanoethyl-1,2,4-triazolyl-(3)]thiophosphoric acid ester 1a 1-Cyanoethyl-semicarbazide 1672 g of semicarbazide hydrochloride is dissolved in 2 liters of water, and neutralised, with cooling, with 600 g of sodium hydroxide in 1 liter of water. After the addition dropwise of 795 g of acrylonitrile, the mixture is heated for 7 hours at 80° C. and then allowed to stand for 4 hours at 0° C.; the precipitated crystalline product is subsequently filtered off, and dried under vacuum. There is obtained 1152 g of white product having a melting point of 125°–128° C.

Analysis: Calculated: 37.5% C; 6.3% H; 43.7% N. Found: 37.2% C; 6.3% H; 43.4% N.

1b 1-Cyanoethyl-3-hydroxy-1,2,4-triazole 512 g of 1-cyanoethyl-semicarbazide in 1990 ml of orthoformic acid ethyl ester is heated for 45 minutes at 110° C. 900 g of the resulting ethanol is distilled off at a temperature of between 110° and 130° C. After cooling to 20° C., the precipitated crystalline product is filtered off, washed with ether, and dried under vacuum. There is obtained 530 g of white product having a melting point of 182°–184° C.

Analysis: Calculated: 43.5% C; 4.35% H; 40.5% N. Found: 43.4% C; 4.4% H; 41.0% N.

1c

O,O-Diethyl-O-[1-cyanoethyl-1,2,4-triazolyl-(3)]-thiophosphoric acid ester 27.6 g of 1-cyanoethyl-3-hydroxy-1,2,4-triazole and 27.6 g of potassium carbonate in 1000 ml of methyl ethyl ketone are refluxed for 2 hours. After an addition dropwise of 37.6 g of diethylthiophosphoric acid chloride at 40° C., the mixture is again refluxed for 2 hours, and is then allowed to stand for 15 hours at 20° C. The salts are filtered off and the filtrate is concentrated in vacuo. The oily residue is chromatographed through silica gel with methyl ethyl ketone as the eluant. There is obtained 55.6 g of oily compound of the formula

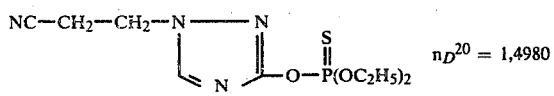  $n_D^{20} = 1.4980$

Analysis: Calculated: 37.2% C; 5.2% H; 19.3% N; 11.0% S. Found: 37.4% C; 5.3% H; 18.2% N; 11.4% S.

The following compounds are prepared in an analogous manner:

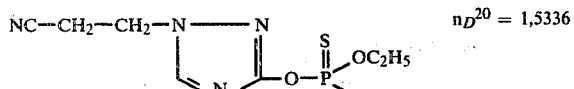 $n_D^{20} = 1.5336$

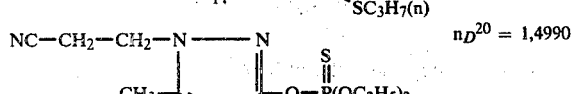 $n_D^{20} = 1.4990$

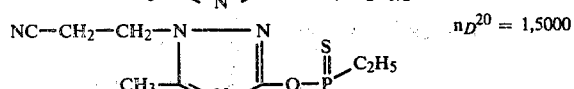 $n_D^{20} = 1.5000$

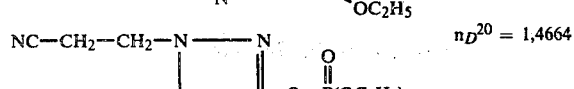 $n_D^{20} = 1.4664$

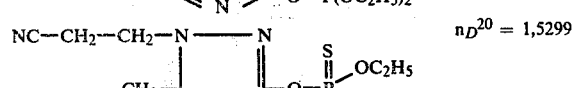 $n_D^{20} = 1.5299$

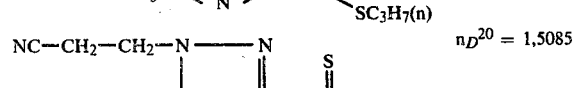 $n_D^{20} = 1.5085$

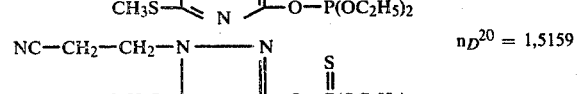 $n_D^{20} = 1.5159$

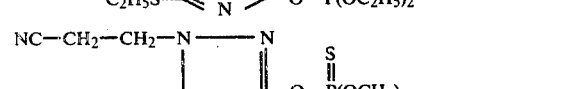

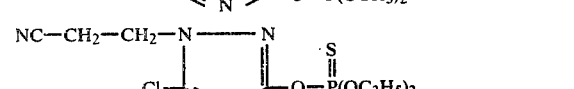

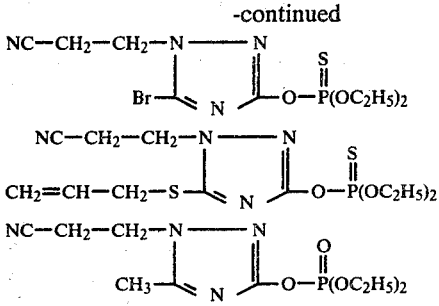

EXAMPLE 2

(A) Insecticidal Stomach Poison Action

Cotton plants were sprayed with a 0.05% aqueous active-substance emulsion (obtained from a 10% emulsifiable concentrate).

After the drying of the resulting coating, *Spodoptera littoralis* or *Heliothis virescens* larvae L₃ were placed onto the cotton plants. The test was carried out at 24° C. with 60% relative humidity.

Compounds according to Example 1 exhibited in the above test a good insecticidal stomach poison action against *Spodoptera littoralis* and *Heliothis virescens* larvae.

(B) Systemic Insecticidal Action

In order to determine the systemic action, rooted bean plants (*Vicia faba*) were placed into a 0.01% aqueous active-substance solution (obtained from a 10% emulsifiable concentrate). After a period of 24 hours, bean aphids (*Aphis fabae*) were placed onto the parts of the plant above the soil. The insects were protected by a special device from the effects of contact and of gas. The test was carried out at 24° C. with 70% relative humidity.

In the above test, compounds according to Example 1 exhibited a systemic action against *Aphis fabae*.

EXAMPLE 3

Action against *Chilo suppressalis*

Rice plants of the type Caloro were planted, 6 plants per pot, in plastic pots having a top diameter of 17 cm, and grown to a height of about 60 cm. Infestation with *Chilo suppressalis* larvae (L₁; 3–4 mm long) was carried out 2 days after application of the active substance in granular form (amount applied=8 kg of active substance per hectare) to the paddy water. The evaluation of the insecticidal action was made 10 days after application of the granules.

Compounds according to Example 1 were effective against *Chilo suppressalis* in the above test.

EXAMPLE 4

Acaricidal Action

*Phaseolus vulgaris* (plants) were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no running-off of the spray liquor. An assessment was made after 2 to 7 days, by examination under a binocular, of the living and of the dead larvae, adults and eggs, and the results were expressed as percentages. The treated plants were kept during the "holding time" in greenhouse compartments at 25° C.

Compounds according to Example 1 were effective in the above test against adults, larvae and eggs of *Tetranychus urticae*.

EXAMPLE 5

Action against Soil Nematodes

In order to test the action against soil nematodes, the active substances were added, in the concentration stated in each case, to soil infested with root-gall-nematodes (*Meloidogyne arenaria*); the whole was then intimately mixed. In the one test series, tomato seedlings were planted immediately after preparation of the soil in this manner, and in the other test series tomatoes were planted after a waiting time of 8 days.

For an assessment of the nematocidal action, the galls present on the roots were counted 28 days after planting and sowing, respectively.

Active substances according to Example 1 exhibited in this test a good action against *Meloidogyne arenaria*.

We claim:
1. A compound of the formula

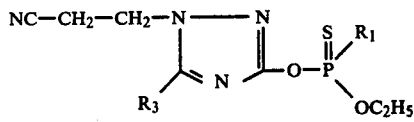

wherein
R$_1$ represents ethyl, ethoxy or n-propylthio, and
R$_3$ represents hydrogen, methyl, methylthio or ethylthio.

2. The compound according to claim 1 of the formula

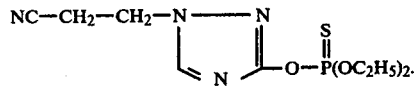

3. The compound according to claim 1 of the formula

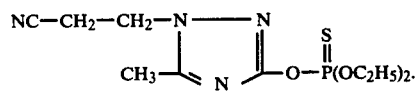

4. The compound according to claim 1 of the formula

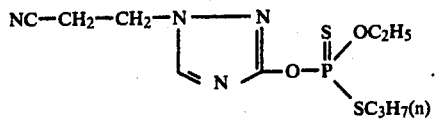

5. The compound according to claim 1 of the formula

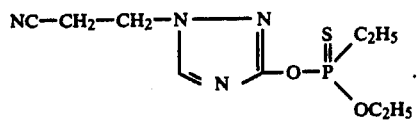

6. The compound according to claim 1 of the formula

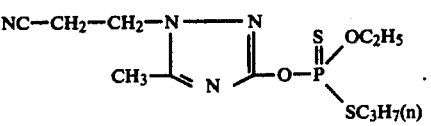

7. The compound according to claim 1 of the formula

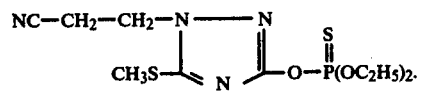

8. The compound according to claim 1 of the formula

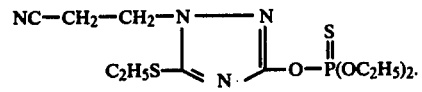

9. The compound of the formula

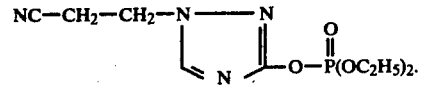

10. A compound of the formula

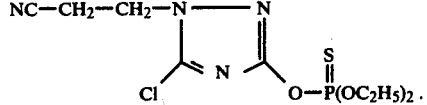

* * * * *